United States Patent [19]
Bittner et al.

[11] Patent Number: 5,515,871
[45] Date of Patent: May 14, 1996

[54] HOLLOW NEEDLE FOR MEDICAL USE AND A LASER METHOD FOR MANUFACTURING

[75] Inventors: Vladimir Bittner, Bern; Roger Dekumbis, Zürich-Oerlikon, both of Switzerland

[73] Assignee: Sulzer Brothers Ltd., Winterthur, Switzerland

[21] Appl. No.: 332,602

[22] Filed: Oct. 31, 1994

Related U.S. Application Data

[63] Continuation of Ser. No. 838,773, Mar. 10, 1992, abandoned.

[30] Foreign Application Priority Data

Sep. 28, 1990 [CH] Switzerland ............... 03131/90

[51] Int. Cl.⁶ ............................................. A61B 19/00
[52] U.S. Cl. ..................... 128/898; 604/239; 604/264; 604/274
[58] Field of Search ...................... 604/272–274, 604/239, 264, 187, 164; 606/167, 222; 128/753, 754, 763; 451/28, 61

[56] References Cited

U.S. PATENT DOCUMENTS

| | | | |
|---|---|---|---|
| 2,717,599 | 9/1955 | Huber | 604/274 |
| 3,064,651 | 11/1962 | Henderson | 604/274 |
| 4,759,746 | 7/1988 | Straus | 604/272 |
| 4,808,170 | 2/1989 | Thornton et al. | 604/274 |
| 4,838,877 | 6/1989 | Massau | 604/272 |

FOREIGN PATENT DOCUMENTS 0620780  3/1949  United Kingdom ............... 604/274

*Primary Examiner*—C. Fred Rosenbaum
*Assistant Examiner*—Ronald K. Stright, Jr.
*Attorney, Agent, or Firm*—Townsend and Townsend and Crew

[57] ABSTRACT

The hollow needle (1) for medical use comprises a duct (10), which usually contains an aperture (11) which is elliptic or similar to an ellipse. The edge (14) of this aperture (11) is rounded by melting in the converging part (14') when regarded from the point (1') of the hollow needle (1). The process for rounding the edge (44) by melting uses a laser (45) which is pulsated or operates continuously, in the effective range (45') of which the part (44') to be rounded of the edge (44) lies.

12 Claims, 2 Drawing Sheets

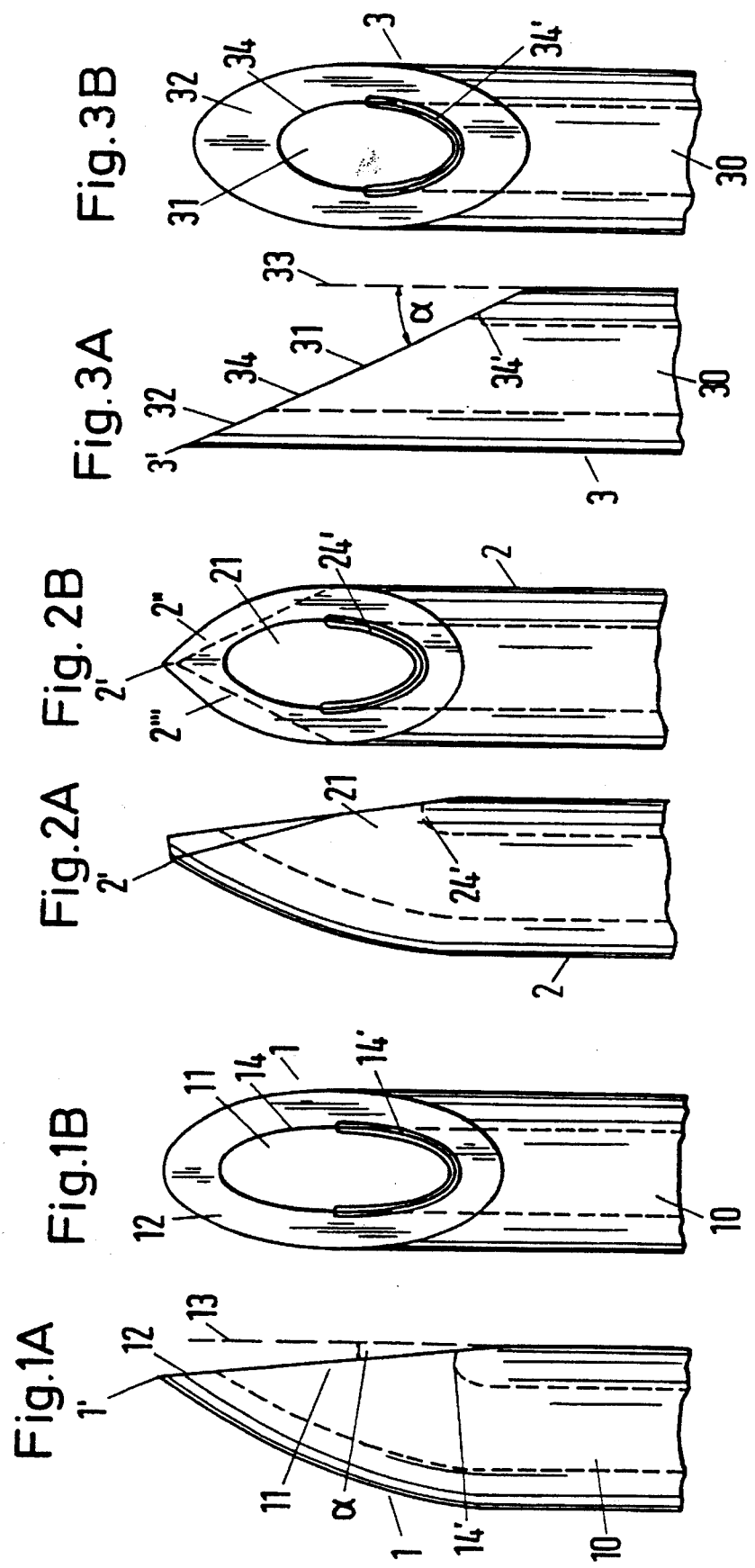

HOLLOW NEEDLE FOR MEDICAL USE AND A LASER METHOD FOR MANUFACTURING

This is a Continuation of application Ser. No. 08/838,773, filed Mar. 10, 1992, now abandoned.

BACKGROUND OF THE INVENTION

The invention relates to a hollow needle having a duct, which comprises an aperture in the region of the needle point. Such needles are used in medicine, for example for injecting and for aspirating, such as the introduction of fluids. The invention also relates to a method for the manufacture of such hollow needles.

The points of conventional hollow needles, such as injection cannulae, are, in simple terms, sharply ground steel tubes. A sharp outer bevel edge, which permits a smooth injection technique, is produced by bevel grinding, for example. However in this case a rear bevel cutting edge, when seen in the direction of puncture, which is just as sharp, is simultaneously produced on the inside of the cannula, i.e. on the edge of the duct, the inner eye, and this can result in skin and tissue lying beneath it being punched out and getting inside the injection cannula.

This may result in the needle duct becoming blocked, in sensitive tissue structures which do not regenerate easily, such as nerve fibers, being damaged, and/or in infected pieces of skin which have been punched out being transmitted into deeper or other tissue structures or layers, and this can result in syringe abscesses.

The shortcomings of the conventional needle point are known. As early as 1891 H. I. Quincke described an improved spinal needle named after him, which is still used today for lumbar puncture. Quincke's spinal needle has a precisely adapted guide (obturator/filling body/insertion rod), which protects the inner lumen of the injection cannula from the ingress of punched out material, e.g. tissue or membrane material. After puncture, the guide is removed, and the liquor fluid can be drawn up without any problems.

In 1898 during the spinal anaesthesia performed for the first time as a self-experiment, A. Bier recognized that the loss of liquor fluid through the puncture wound in the dura/arachnoidea (also called meninges, or the meninx or spinal meninx) can result in a severe postspinal headache. The frequency of postspinal headache is dependent on the diameter of the needle and the type of needle point, together with the age, sex and individual predisposition. In 1922 R. Hoyt pointed out the significance of needle diameters and described the two needle technique, in which a thicker needle is firstly inserted as an "introducer" (insertion aid), and a smaller needle is advanced through this introducer right into the subarachnoid space. The puncture wound of the dura/arachnoidea remains limited by this, and the headache rate is reduced. In 1926 H. M. Greene described a "round ground" (plain ground) needle point, which carefully forces the fibers of the dura and arachnoidea apart, but does not split them, as is the case with the conventional Quincke needle having the sharp outer bevel edge. A further development of the "atraumatic spinal needle" was described in 1951 by Hart and Whitacre: a needle with a closed needle point like the point of a pencil with a lateral aperture into said point. This needle was further improved by Sprotte in 1987 by enlarging the lateral aperture so as to prevent a nozzle effect when injecting the local anaesthetic into the liquor.

In 1944 E. B. Tuohy described the method of continuous spinal anaesthesia. For puncture he used a so-called Huber cannula, an injection cannula having a curved point. The curve is formed so that the bevel plane of the needle point can be guided parallel to the cannula. This results in that the rear bevel cutting edge of the cannula point can be hidden behind the curve, and as a result the risk of punching out tissue is reduced, but not eliminated. In 1957 R. S. Wagner Jr. improved the Huber cannula by reducing the bending radius at the needle point and as a result he achieved better control of the bevel plane parallel to the cannula and reduced the length of the bevel eye. The more precise positioning of the needle point was achieved by this. In 1958 P. A. Cheng modified the curved needle point again by blunting the front bevel cutting edge and guiding the bevel plane with a slight angle to the cannula plane. However in all the above-specified designs the rear bevel cutting edge remains sharp. Therefore to reduce the risk of tissue being stamped out during puncture, an adapted guide, which covers the rear bevel cutting edge, i.e. the edge of the aperture, is introduced into the needle.

In 1989 H. Haindel and H. Müller described a cannula having a concave bevelled point, which does not punch out tissue to a great extent (Biomed. Technik, 34 (1989), 79–84), in which the rear edge of the aperture of the duct is blunted with a special glass bead ray treatment. The bead ray treatment can result in residue in the duct, which is very difficult to remove. The bead ray treatment, which does not permit a specific and selective treatment of the rear, inner bevel cutting edge, may result in only an unsatisfactory inner rounding of the edge of the aperture being achieved.

The use of this cannula is recommended for the protection of the silicone membrane of portable systems (to receive the injection fluid from membrane-sealed containers, the membrane is perforated with the needle/the container can be implanted). With its use in other puncture techniques (anaesthesia, neurosurgery, radiology) in tissue which is less consistent than silicone rubber, parts of tissue are punched out. This is the case in particular when puncturing nerve tissue, which has less inherent elasticity and consistency.

A cavity needle having a point in the shape of a pencil point, in which the cannula aperture is laterally mounted in the cylindrical part, is referred to as "Sprotte needle". The aperture of the duct is relatively far away from the point in the Sprotte needle. The Sprotte needle is also used with a guide so as to prevent the penetration of tissue particles into the cannula aperture. Therefore it is practically impossible to use it during punctures which have to guarantee a free backflow of fluid through the needle during puncture. The lateral aperture of the duct, the cannula eye, represents a weak point in the cannula and there is a risk of the cannula bending or even the hollow needle breaking when it comes into contact with bone.

From the medical point of view, the punching out of tissue particles is associated with an increased tissue trauma for the patient and is therefore undesirable. This is particularly the case if the cannula has to be introduced into tissue which does not easily regenerate, such as nerves (conduction anaesthesia) or brain (neurosurgery).

When steroids are injected, which impair the immune defense system, the transmission of stamped out particles of skin into other tissue layers can result in dreaded syringe abscesses. The location and positioning of cannulae in tissue structures, in which the position of the hollow needle is verified and controlled by means of fluid which freely flows back (blood, liquor, lymph, synovial fluid, bile, discharges, accumulation of pus, etc.), is hampered if the lumen/the duct is restricted or even blocked by tissue parts or in any other way. A multiple puncture is the necessary consequence, frequently associated with tissue trauma and an increase in pain for the patient.

SUMMARY OF THE INVENTION

The present invention provides an improved hollow needle, which always contains an open lumen, even in multiple use, i.e. with which the duct is not blocked or contaminated by flakes of membranes and/or tissue residue punched out from the puncture duct.

In the fluid phase, during the laser treatment, because of the surface tension, the edge to be rounded by melting, which at first is sharp, assumes a blunt shape, which is preferably rounded all over and does not cut, in which the edge of the duct or the cannula solidifies again.

The method for manufacturing the hollow needle, enables the edge of the duct to be melted to the required extent by precisely metering the energy of the laser beam or of the effective part of the laser beam, in which case the edge is rounded not only on the outside, but also on the inside of the duct.

By using laser beams for the rounding process, it is possible to work with hollow needles made from varied materials and having varied dimensions. In particular, with this method it is possible to round the edges of the ducts of hollow needles having an external diameter of less than 0.5 mm, for example in the range of 0.5 to 0.2 mm. Similarly, in the case of multiple cannulae—it is possible to round the edges of the apertures of the ducts of multi-duct hollow needles by melting.

Gas or solids lasers, for example $CO_2$ or Nd-YAG lasers, which are pulsed, may be suitable laser sources. The hollow needles to be treated can be conveyed by a transport device to the beat of the laser pulses to its region of operation. In this connection it should be ensured that the edge to be rounded is located in the correct focal spot or operating point of the laser beam during the pulse.

However it is conceivable that the laser be operated continuously and the period of dwell of the regions of the duct edge to be rounded be such that the desired rounding of the edge is achieved.

With pulsed lasers for hollow needles having an external diameter which is approximately one mm or less, pulses having an overall pulse energy of approximately 0.02 to 20 Joules are normally adequate. In this case the diameter of the working range or the operating site of the laser beam is approximately three times as large as the external diameter of the hollow needle.

The edges are advantageously rounded by melting with the use of a protective gas, such as nitrogen, argon or helium, for example. The condition of the part to be rounded of the duct edge of the hollow needles can be influenced with the protective gas, which is simultaneously used as a cooling gas.

The hollow needle for medical use comprises a duct, which usually comprises an aperture which is elliptic or similar to an ellipse. The edge of this aperture is rounded by melting in the converging part, when viewed from the point of the hollow needle. The process for rounding the edge uses a laser which operates in pulses or continuously, in the working range of which the part of the edge to be rounded lies.

BRIEF DESCRIPTION OF THE DRAWINGS

FIGS. 1A and 1B show the needle point of a hollow needle having a curved point and a curved duct in front and lateral elevation;

FIGS. 2A and 2B show the point of a hollow needle with a facetted cut in front and lateral elevation;

FIGS. 3A and 3B show a hollow needle with a straight duct and an obliquely sharpened needle point in front and lateral elevation.

DESCRIPTION OF THE PREFERRED EMBODIMENTS

Figure 4A:
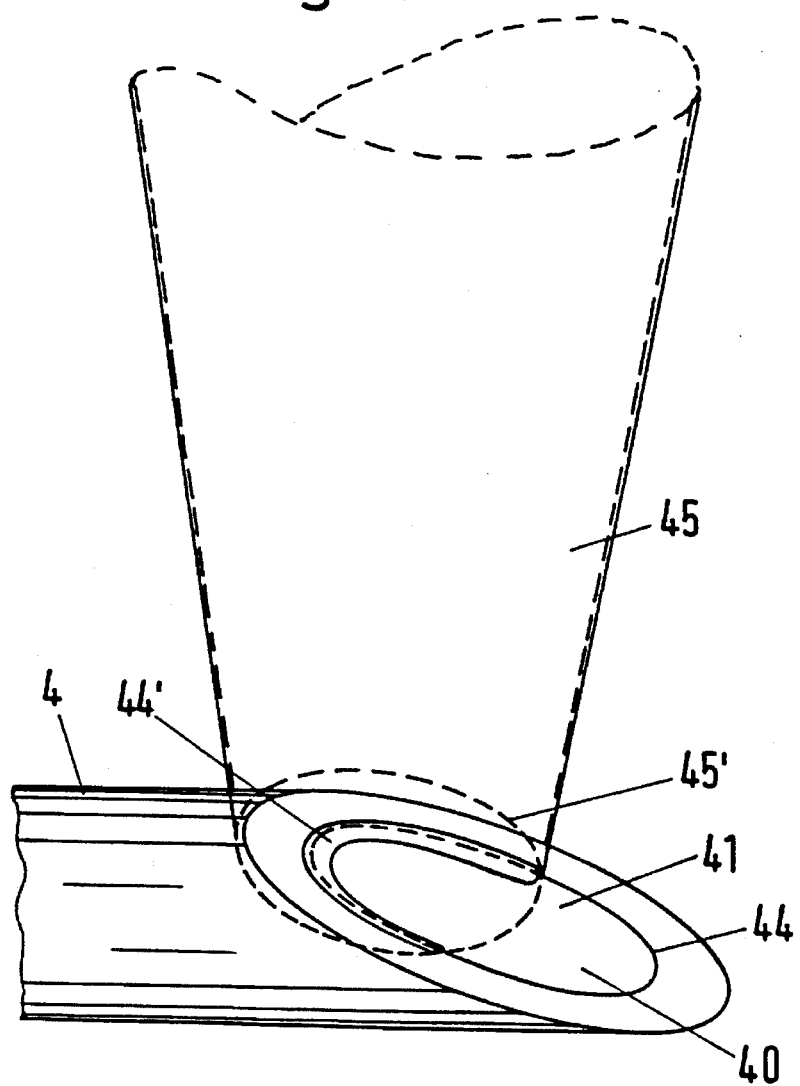
FIGS. 4A and 4B show a perspective view and a lateral view of the arrangement of a laser beam and the point of the hollow needle during the rounding operation performed by melting.

The point 1' of the hollow needle 1 or cannula 1, which is shown greatly enlarged in FIGS. 1A and 1B, is curved. The duct 10 is also curved in the region of the elliptic aperture 11. The aperture 11 opens into the sharpened plane 12, which with the extension 13 of the shell line and consequently also with the axis of the hollow needle 1, forms an angle $\alpha$ of approximately 6°. A concave or convex surface could also be provided instead of the sharpened plane 12. The edge 14 of the aperture 11 of the duct 10 is rounded by melting in the rear converging part 14' when viewed from the point 1' of the hollow needle 1 (its size is greatly exaggerated). Of course it is also possible to round other regions or the entire edge 14 of the aperture 11 of duct 10 by melting. The external bending radius of the point 1' of such needles 1 is advantageously approximately twice the external diameter of hollow needle 1. The external diameter of hollow needle 1 may also lie in the ultra-thin range of just a few tenths of a millimeter, e.g. 0.3 mm, but also in the thick needle range of over one millimeter.

The point 2' of the hollow needle 2 shown in FIGS. 2A and 2B is constructed in the region of the point 2' with the two facet-like planes 2" and 2'". This facetted surface improves the puncture properties of the hollow needle 2. The hollow needle 2 is also curved and is constructed similar to the point 1' of the hollow needle 1 shown in FIGS. 1A and 1B. In particular the aperture 21 also comprises a region 24 rounded by melting.

The point 3' of the straight hollow needle 3 comprises a bevel surface 32, into which the aperture 31 of the duct 30 opens. Here too the elliptic edge 34 of aperture 31 of duct 30 is rounded by melting in the rear, converging part 34' when viewed from the point 3' of hollow needle 3 (its size is greatly exaggerated). The angle $\alpha$ of the extension 33 to the plane of the bevel surface is in the region of approximately 30°, for example. This embodiment of the hollow needle is suitable for ultra-thin cannulae having an external diameter of 0.5 mm and less, for example.

Figure 4B:
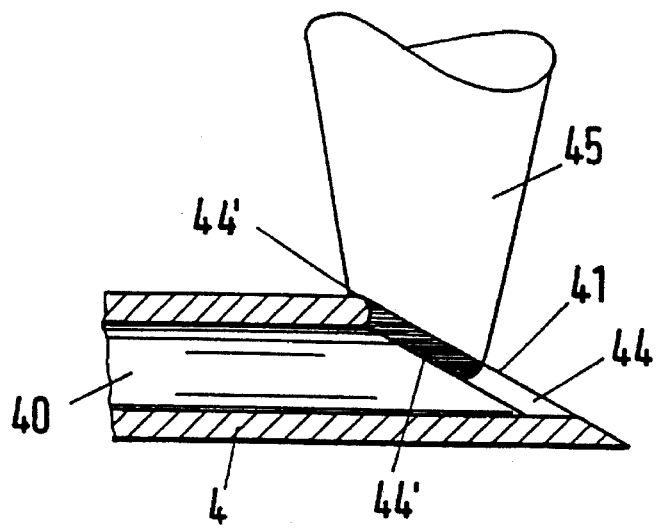

Finally FIG. 4A and FIG. 4B show the laser beam 45 and its effective range 45' with the hollow needle 4 at the moment of rounding by melting. The elliptic edge 44 of the aperture 41 of duct 40 is melted by the laser pulse, and the required rounded part 44', which is blunt and consequently does not cut, is formed. The type, i.e. the cross section of the part 44' of the edge 44 rounded by melting, can be influenced and varied in exactly the same way as its size is, with the energy, the diameter of the operative or effective range 45' and the protective gas conditions, for example. The rounding of the edge 44 of the hollow needle 4, which would be mounted on a transport device (not shown), could also be achieved and influenced with a continuously working laser with an appropriate period of dwell of the part 44' to be rounded of edge 44.

What is claimed is:

1. A method of manufacturing a hollow needle adapted to puncture live tissue in connection with a medical procedure, the method comprising the steps of providing a tubular needle made of metal having a face extending across the needle forming a pointed needle end and defining an aperture bounded by an intersection edge between the face and an interior surface of the needle; providing a laser; directing a laser beam generated by the laser against a portion of the intersection edge furthest removed from the needle end; melting the metal of the needle defining said portion with energy transmitted by the laser beam to thereby generate a rounded surface of melted metal between the face and the interior needle surface along said portion; thereafter discontinuing the step of directing the laser beam at said portion; and cooling the melted metal to solidify it to thereby form a rounded surface of solid metal between the face and the interior surface of the needle.

2. A method according to claim 1 including the step of controlling the duration during which the laser beam is directed at said portion of the edge.

3. A method according to claim 2 wherein the step of controlling comprises the step of pulsing the laser.

4. A method according to claim 2 wherein the step of controlling comprises the step of causing relative movement between the needle and the laser to thereby move said portion into and out of the laser beam, and controlling the duration during which said portion is in the laser beam.

5. A method according to claim 1 including the step of limiting a diameter of the laser beam at said portion of the intersection edge to three times the diameter of the needle.

6. A method according to claim 5 including the step of maintaining an atmosphere of a protective gas at said portion of the intersection edge during the directing step and while the metal is melted.

7. A method according to claim 1 including the step of limiting a diameter of the laser beam to between 0.5 and 3.0 mm.

8. A method according to claim 1 wherein the step of directing the laser beam includes the step of subjecting said portion of the intersection edge to energy generated by the laser in the range of between 0.02 and 20 Joules.

9. A method according to claim 1 including the step of selecting the protective gas from the group consisting of nitrogen, argon and helium.

10. A method for manufacturing a hollow needle adapted to puncture live tissue in connection with a medical procedure, the method comprising the steps of:

providing a hollow needle made of metal and having an end face extending across the needle defining a pointed needle end, a needle aperture, and a sharp edge along an intersection between the face and an interior surface of the needle;

providing a laser for generating a laser beam;

directing the laser beam to a portion of the edge furthest removed from the pointed end and subjecting metal of the needle defining the edge over said portion to energy in the range of between 0.02 and 20 Joules to thereby melt the metal along said portion of the edge;

permitting surface tension of the melted metal to form a smooth, round melted metal surface between the face and the interior needle surface;

discontinuing the directing step; and cooling the melted metal while said surface tension maintains said rounded surface to thereby solidify the melted metal and provide the needle with a smooth, rounded solid metal surface between the face and the interior surface along said portion of the edge.

11. A method according to claim 10 wherein the step of directing includes the step of directing the laser beam against the entire sharp edge between the face and the interior needle surface.

12. A method according to claim 10 wherein the step of directing comprises the step of directing the laser beam against no more than about one-half of the length of the sharp edge between the face and the interior needle surface.

* * * * *